United States Patent
Grossman

(10) Patent No.: US 7,392,688 B2
(45) Date of Patent: Jul. 1, 2008

(54) LIQUID REACTION MASS FOR HIGH-G SIMULATION

(75) Inventor: Owen Grossman, Golden Valley, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/908,943

(22) Filed: Jun. 1, 2005

(65) Prior Publication Data

US 2006/0272435 A1    Dec. 7, 2006

(51) Int. Cl.
*G01M 7/00* (2006.01)

(52) U.S. Cl. .................................................. 73/12.08

(58) Field of Classification Search ............. 73/12.08, 73/665, 671
See application file for complete search history.

(56) References Cited

U.S. PATENT DOCUMENTS

| 2,698,105 | A | * | 12/1954 | Mackas | 73/12.08 |
|---|---|---|---|---|---|
| 3,729,980 | A | * | 5/1973 | Johnson et al. | 73/12.08 |
| 4,010,631 | A | | 3/1977 | Pollin | |
| 4,557,143 | A | | 12/1985 | Pollin | |
| 4,566,314 | A | * | 1/1986 | Thurston | 73/54.09 |
| 4,610,256 | A | * | 9/1986 | Wallace | 600/488 |
| 4,884,456 | A | | 12/1989 | Meline et al. | |
| 5,138,884 | A | * | 8/1992 | Bonavia | 73/662 |
| 5,355,456 | A | * | 10/1994 | Osofsky | 392/342 |
| 5,471,877 | A | * | 12/1995 | Brown | 73/571 |
| 5,487,298 | A | | 1/1996 | Davis et al. | |
| 5,550,792 | A | * | 8/1996 | Crandall et al. | 367/155 |
| 5,918,265 | A | * | 6/1999 | Oertel et al. | 73/37 |
| 5,987,741 | A | * | 11/1999 | Banakis et al. | 29/842 |
| 6,655,190 | B2 | | 12/2003 | Grossman et al. | |
| 2002/0152816 | A1 | * | 10/2002 | Kim | 73/715 |
| 2003/0074949 | A1 | * | 4/2003 | Albertini et al. | 73/12.08 |
| 2004/0004904 | A1 | * | 1/2004 | Betts | 367/3 |
| 2005/0126287 | A1 | | 6/2005 | Malametz | |

* cited by examiner

*Primary Examiner*—Robert R Raevis
(74) *Attorney, Agent, or Firm*—Black Lowe & Graham PLLC

(57) ABSTRACT

An apparatus for simulating a dynamic high-g environment that includes a test specimen, an incompressible liquid situated adjacent to the test specimen, and a device for creating a dynamic force on the test specimen. In one embodiment, the device for creating a dynamic force includes a vibration actuator that creates a force by creating movement between the test specimen and the incompressible liquid.

13 Claims, 3 Drawing Sheets

LIQUID REACTION MASS FOR HIGH-G SIMULATION

FIELD

The present invention relates generally to acceleration testing of products and/or components parts, and more specifically, to the simulation of high acceleration forces on products and/or component parts.

BACKGROUND

It is often desirable to test products and/or their component parts under conditions that are similar to those expected in the field. The test results may be used to help ensure that the products and/or their component parts will function properly in the field. For some applications, it is difficult to properly test the products and/or component parts, sometimes because of the extreme conditions for which they are intended to be used. For example, testing projectiles and/or components of such projectiles, such as circuit cards, during conditions of a ballistic event in a controlled and reproducible manner can be difficult. Similarly, testing acceleration sensors and/or cards during conditions of an automobile crash can be difficult. These are just a few examples.

The testing of components for use in a projectile would ideally include simulation of accelerative forces that are similar to those that are expected during actual service in the field. However, the associated long duration, high acceleration environment of ballistic applications, such as the firing of a gun, can typically not be adequately simulated in a laboratory environment. The ruggedness and reliability of many components generally cannot be qualitatively, quantitatively, or comparatively evaluated except under conditions which simulate their actual flight experience without the terminal destruction which would be experienced by actual flight. Not being able to simulate/test these high-g forces has presented some design challenges.

A typical method of simulating forces that are experienced by a projectile include using an "air gun" that accelerates a projectile by air pressure in a confined tube of suitable diameter. However, this and many other previous methods have a maximum force and/or duration that can be produced and simulated. For example, an air gun may be capable of producing levels up to 20,000 G's, but at these force levels, the duration of the event is typically less than a millisecond or so. For many ballistic applications, such as the firing of a gun, as well as other high-g applications, the events may extend over 10 milliseconds or more. Thus, it may be desirable to simulate relatively large forces over a relatively longer duration.

SUMMARY

The following summary of the invention is provided to facilitate an understanding of some of the innovative features unique to the present invention and is not intended to be a full description. A full appreciation of the invention can be gained by taking the entire specification, claims, drawings, and abstract as a whole.

The present invention relates generally to the simulation of relatively high acceleration forces on components or component parts. In one illustrative embodiment, an apparatus for simulating such environments includes a test specimen, such as a circuit card, an incompressible liquid situated adjacent to the test specimen, and a device for creating a dynamic high-g event on the test specimen. In one case, the device for creating the dynamic high-g event may include a vibration actuator that creates a force between the test specimen and the liquid. The vibration actuator may create such a force by moving (e.g. vibrating) the test specimen toward the incompressible liquid. In some cases, and to help increase the force that is exerted on the test specimen in response to movement by the vibration actuator, a reaction mass may be situated opposite the incompressible liquid. In some cases, the incompressible liquid itself may function as, and/or contribute to, the reaction mass. In another illustrative embodiment, the device for creating the dynamic high-g event may be a dynamic hydraulic pressure supply that creates a pressure pulse or the like in the incompressible liquid, and toward the test specimen.

An illustrative method for simulating a high-g environment may include providing a test specimen mounted on a mounting structure, providing an incompressible liquid adjacent to one side of the test specimen, and creating a dynamic high-g force on the test specimen. In some cases, the dynamic high-g event is created by a vibration actuator that may create vibratory movement between the test specimen and the incompressible liquid. In other embodiments, the dynamic high-g event may be created by a dynamic hydraulic pressure pulse in the incompressible liquid, or in any other suitable manner.

BRIEF DESCRIPTION

DETAILED DESCRIPTION

Figure 1:
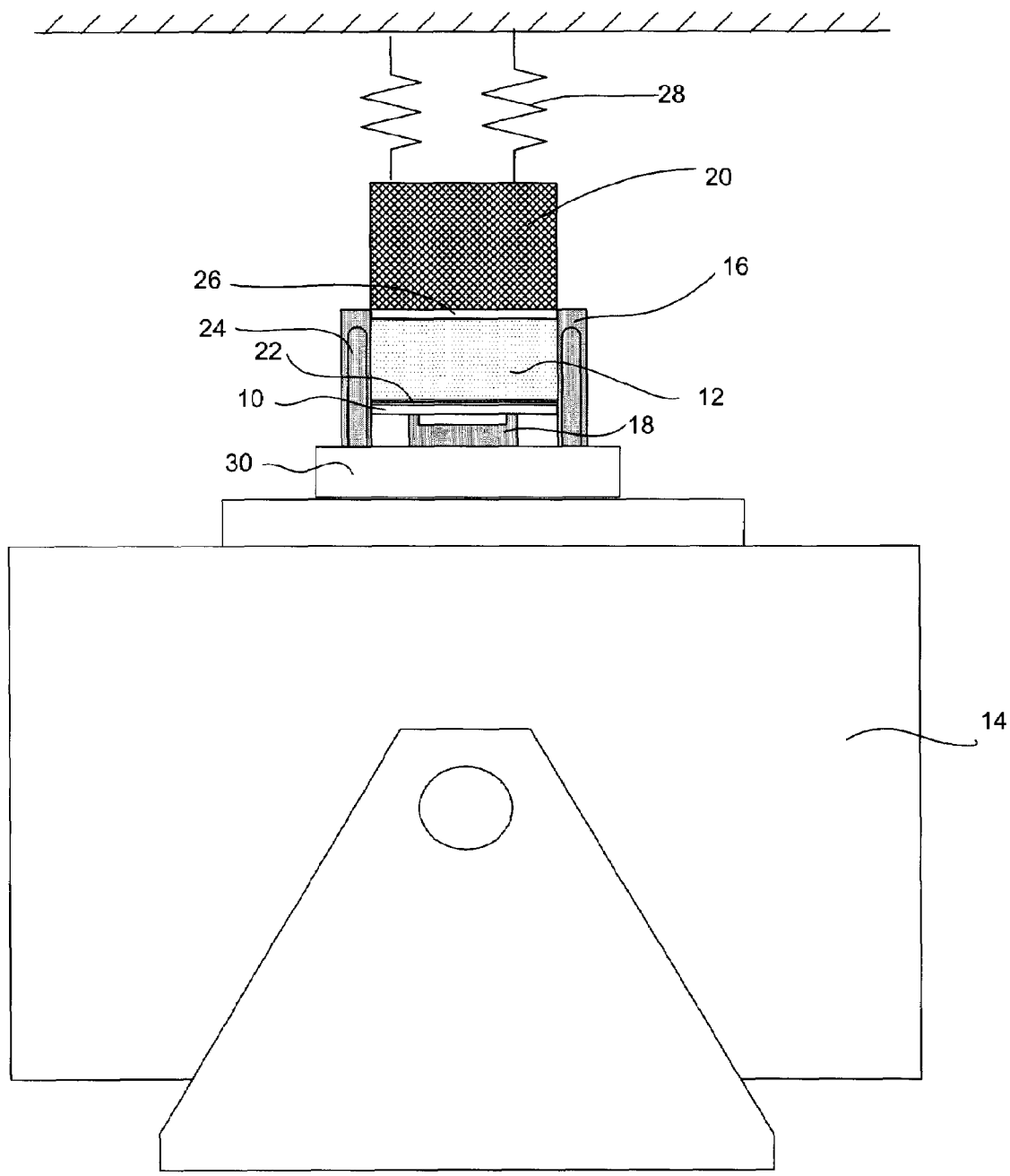
FIG. 1 is a schematic diagram of an illustrative embodiment of a high-g simulator.

The following description should be read with reference to the drawings wherein like reference numerals indicate like elements throughout the several views. The detailed description and drawings show several embodiments which are meant to be illustrative of the claimed invention.

FIG. 1 is a schematic diagram of an illustrative embodiment of a high-g simulator. The illustrative high-g simulator may be able to simulate real world high-g force levels on a test specimen 10 in a measured environment. Under some circumstance, the simulator may be able to simulate greater than 2,000 g's, and in some cases thousands or tens of thousands of g-forces on the test specimen. In some cases, the simulation of real world high-g events may correspond to the firing of a printed wiring board from a gun or cannon, wherein the gunshot may be approximately a 10 millisecond pulse creating g forces in the tens of thousands of g's. However, it is contemplated that any suitable gunshot pulse length and/or force level may be simulated. Also, the high-g simulator may be used to simulate other high-g events, such as car crash events or the like.

The illustrative embodiment includes a test specimen 10, a mounting structure 18 for mounting the test specimen 10, an incompressible liquid 12 situated above and adjacent to the test specimen 10, and an actuator device (e.g. shaker) for creating a dynamic high-g event on the test specimen 10. In some cases, the test specimen 10 may be a printed wiring board or a circuit card, but it is contemplated that other products or components may be similarly tested. More generally, the test specimen 10 may be any specimen that is subject to relatively high-g forces, high acceleration environments, or high stress levels, as desired. In some cases, the weight of the test specimen (e.g. printed wiring board) may be in the range of one twentieth of a pound to one tenth of a pound. However, the weight of the test specimen 10 may be any weight as required or desired for the particular application at hand.

The incompressible liquid 12 may be water based, hydraulic fluid based, or any other suitable based liquid 12 as desired, including a gel form. The illustrative incompressible liquid 12 may provide a reaction force on the test specimen 10. In some cases, the reaction force may be in "reaction" to the movement of the actuator 14, as further described below. In some cases, the liquid 12 may have a surface area adjacent to the test specimen in the range of 3 to 4 square inches, but it is contemplated that any other suitable surface area may be used as desired for the simulated real world application, as well as on the size and other characteristics of the test specimen 10.

In some cases, the illustrative embodiment may include a diaphragm 26 and/or a membrane 22. In one illustrative embodiment, a diaphragm 26 may be situated on one side of the liquid 12, and a membrane 22 may be situated on the other. In some cases, the diaphragm 26 may be situated between the liquid 12 and a separate reaction mass 20, and the membrane 22 may be situated between the test specimen 10 and the incompressible liquid 12. A containment fixture 16 may be provided to help contain the liquid 12 between the diaphragm 26 and the membrane 22.

Alternatively, or in addition, the liquid 12 may be contained in a bag or the like, where the membrane 22 and diaphragm 26 are different sides of the bag. A containment fixture 16 may still be provided, if desired, to add support to the sides of the bag. The membrane 22 and/or diaphragm 26 made be made of any suitable material, such as a polymer or any other material as desired, which does not impede or substantially impede the transmission of the reaction force from the incompressible liquid to the test specimen 10.

An actuator device 14 may create a dynamic high-g event on the test specimen 10. In some cases, the actuator device 14 may be a vibration actuator, such as a shaker. The vibration actuator 14 may move the mounting structure 18 and thus the test specimen 10 toward and away from the liquid 12, thus creating a force between the test specimen 10 and the liquid 12. In some cases, the actuator device may move the incompressible liquid 12 relative to the test specimen 10 to help create a dynamic high-g event.

In one illustrative embodiment, the actuator device 14 is a shaker. The shaker may be, for example, an electro-dynamic shaker, a hydraulic shaker, a piezoelectric shaker, or any other suitable shaker, as desired. The shaker may generate, for example, about 15,000 pounds of force, about 30,000 pounds, about 50,000 pounds, or any other suitable force, as desired.

Alternatively, the actuator device 14 may be a dynamic hydraulic pressure supply. The dynamic hydraulic pressure supply may create a pulse in, for example, the incompressible liquid 12, which then presents a force on the test specimen 10. In some cases, the dynamic hydraulic pressure supply may be a high frequency dynamic hydraulic pressure supply, but this is not required.

To help increase the force experienced by the test specimen, a reaction mass 20 may be provided. In the illustrative embodiment shown in FIG. 1, the reaction mass 20 is situated opposite the incompressible liquid 12 from the test specimen 10. Under some circumstance, the reaction mass 20 may increase the force on the test specimen 10 for a given force applied by the actuator device 14. Thus, one possible advantage of the reaction mass 20 is that by adding more weight adjacent to the test specimen-liquid interface, a given actuator device 14 may be able to simulate a greater force on the test specimen 10. For example, the force on the test specimen 10 may be the mass of the test specimen and in some cases, the mass of the reaction mass 20, times the G level produced by the actuator device 14. That is, if the mass of the test specimen 10 is 0.1 lb and the gunshot is expected to produce 10,000 G's, then the force acting on the test specimen during the gunshot may be about 1,000 lbs. If a 100 lbs reaction mass is added to the mass of the test specimen, then the actuator device 14 may only need to generate 10 G's to generate a 1,000 lbs force on the test specimen. Thus, the greater the weight of the reaction mass 20, the greater the force that can be simulated by a given actuator device 14. In some cases, the incompressible liquid 12 itself may function, or at least contribute to, the reaction mass 20. In other cases, the reaction mass 20 may be a separate structure, if desired.

The illustrative embodiment shown in FIG. 1 includes a mounting structure 18 situated next to the actuator device 14. The test specimen 10 is mounted in or on the mounting structure 18 in a way that simulates the mounting of the test specimen 10 in actual use. In some cases, the mounting structure 18 and the test specimen 10 may be rigidly attached to the actuator device 14.

In some cases, the test apparatus may be opened and closed to allow the test specimen 10 to be inserted and removed. Springs, such as springs 28, may help raise the reaction mass 20. The liquid 12 may then be removed, and there may be access to the test specimen 10 and mounting structure 18 so that the test specimen 10 may be mounted and un-mounted. In some cases, the containment fixture 16 may include more than one piece including, for example, one or more guide pins 24 that are insertable into a wall of the containment structure. The guide pins 24 may be attached to an head 30 of the actuator device 14, and may help secure the containment fixture 16 to the head 30. Also, the guide pins 24 may make a more rigid support for the containment fixture 16. However, it is contemplated that any method may be used to fix and align the containment fixture 16 with the head 30.

Figure 2:
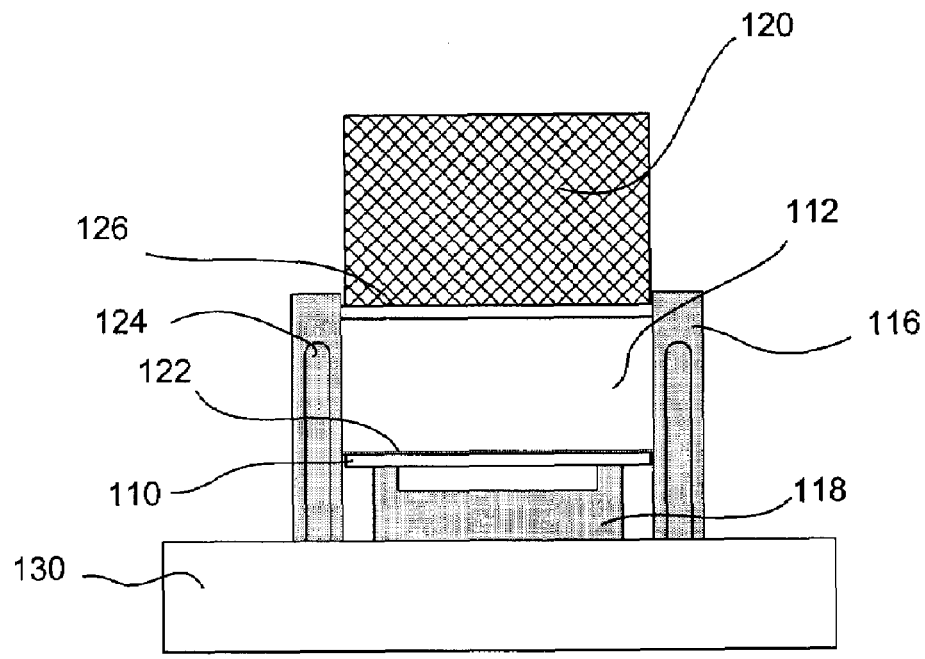
FIG. 2 is a schematic diagram of an illustrative embodiment of a dynamic high-g simulator using a reaction mass.

FIG. 2 is a schematic diagram of another illustrative embodiment of a dynamic high-g simulator using a reaction mass 120. In this illustrative embodiment, the mounting structure 118 may be attached to a shaker head 130. The mounting structure 118 may be adapted to have the test specimen 110 mounted thereon. In some cases, the test specimen 110 may be a circuit card, a printed wiring board, or any other test specimen as desired. The incompressible liquid 112 may be situated so that it is in registration with the test specimen 110, so that any movement of the test specimen 110 may create a force on the liquid 112. In the illustrative embodiment, a containment fixture 116, a membrane 122, and a diaphragm 126 are also provided and situated around the liquid 112.

A reaction mass 120 is provided and engages the diaphragm 126. The reaction mass 120 may add weight to the incompressible liquid 112 creating a greater force on the liquid 112 test specimen 110 interface, resulting in a higher force simulation. The reaction mass 120 may be any mass that adds weight such as a liquid, metal, plastic, or any other suitable material as desired.

Figure 3:
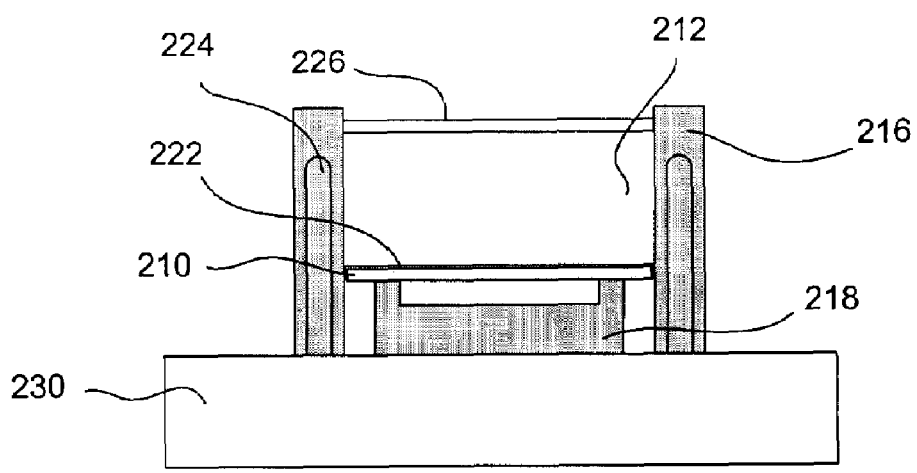
FIG. 3 is a schematic diagram of an illustrative embodiment of a dynamic high-g simulator with the incompressible liquid as a reaction mass.

FIG. 3 is a schematic diagram of an illustrative embodiment of a dynamic high-g simulator with the incompressible liquid 212 used as a reaction mass 220. In this illustrative embodiment, the mounting structure 218 may be attached to a shaker head 230, as shown, and a test specimen 210 may be mounted to the mounting structure 218. The incompressible liquid 212 may be situated so that it is in registration with the test specimen 210, so that any movement of the test specimen 210 may create a force on the liquid 212. In some cases, the illustrative embodiment may include a containment fixture 216, a membrane 222, and a diaphragm 226, which may be situated around the liquid 212. In this illustrative embodiment, the incompressible liquid 212 may function as a reaction mass to create and/or increase the force on the test specimen 210. In some cases, a larger volume of incompressible liquid 212 may be used to create additional force, or a lesser volume may be used to create less force, as desired.

Figure 4:
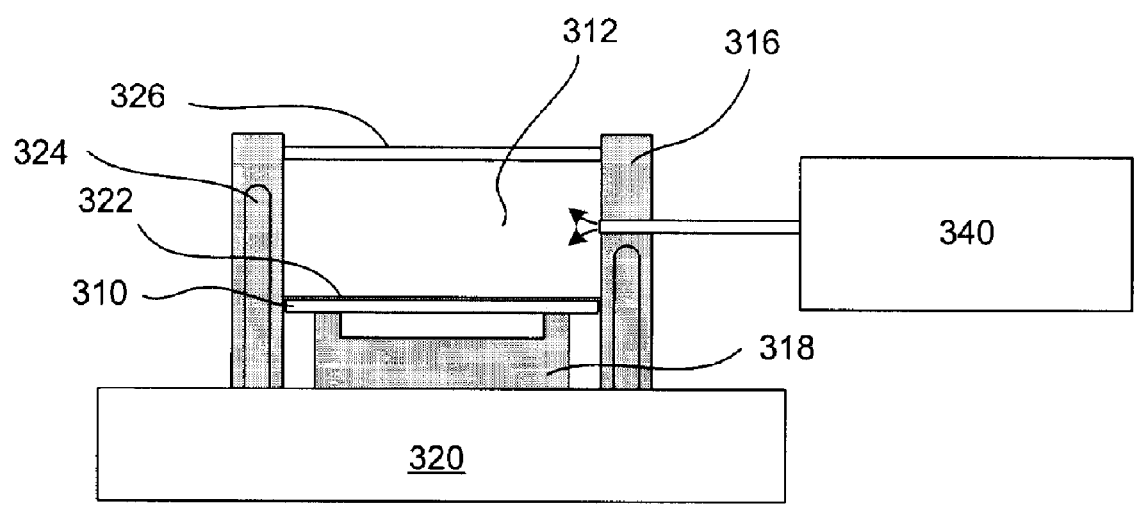
FIG. 4 is a schematic diagram of an illustrative embodiment of a dynamic high-g event using a high frequency dynamic hydraulic pressure supply.

FIG. 4 is a schematic diagram of an illustrative embodiment of a dynamic high-g event using a dynamic hydraulic pressure supply 340. The illustrative embodiment includes an incompressible liquid 312, a diaphragm 326, a membrane 322, a containment fixture 316, a test member 310, a mounting structure 318, and a dynamic hydraulic pressure supply 340. The dynamic hydraulic pressure supply 340 may be a high frequency dynamic hydraulic pressure supply 340, but his is not required.

In this illustrative embodiment, the dynamic hydraulic pressure supply 340 may create a dynamic high-g event. The dynamic hydraulic pressure supply 340 may be in fluid communication with the incompressible liquid 312 in such a way as to create a pressure pulse in the liquid 312. The liquid 312, being in registration and in contact with the test specimen 310, may transmit the pressure pulse to the test specimen 310. This pressure may create a force on the test specimen 310, which simulates a real world high-g event. Similar to the previous embodiments, a reaction mass, such as reaction mass 318 and 320 may be provided to add weight creating a higher pressure at the test specimen 310. The reaction mass 320 may be an incompressible liquid 312 or any other structure that is capable of acting as a reaction mass, as desired.

Having thus described the preferred embodiments of the present invention, those of skill in the art will readily appreciate that yet other embodiments may be made and used within the scope of the claims hereto attached. Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. An apparatus for simulating a dynamic high-g environment on a test specimen having a first side and a second side opposite the first side, said apparatus comprising:
   an incompressible liquid, all of said incompressible liquid of said apparatus situated to be adjacent to only the first side of the test specimem; and
   a mounting structure configured to engage only the second side of the test specimen, the mounting structure operable to maintain a position of the test specimen and substantially support the weight of the test specimen; and
   a device for creating a dynamic pressure event on the test specimen and the incompressible liquid,
   wherein the device for creating a dynamic pressure event is a vibration actuator that vibrates the test specimen relative to the incompressible liquid.

2. The apparatus of claim 1 wherein the device for creating a dynamic event creates movement between the test specimen and the incompressible liquid.

3. The apparatus of claim 1 wherein the test specimen and mounting structure are rigidly attached to the vibration actuator.

4. The apparatus of claim 3 further comprising:
   a membrane situated between the test specimen and the incompressible liquid;
   a diaphragm situated opposite the membrane of the incompressible liquid; and
   a containment fixture situated around the sides of at least a portion of the incompressible liquid.

5. The apparatus of claim 3 further comprising a reaction mass situated opposite the incompressible liquid from the test specimen.

6. The apparatus of claim 5 wherein the reaction mass is a rigid structure.

7. The apparatus of claim 3 wherein the incompressible liquid functions as a reaction mass.

8. The apparatus of claim 1 wherein the incompressible liquid is water based.

9. The apparatus of claim 1 wherein the incompressible liquid is hydraulic fluid based.

10. An apparatus for simulating a dynamic high-g environment on a test specimen having a first side and a second side opposite the first side, said apparatus comprising:
    an incompressible liquid, all of said incompressible liquid of said apparatus situated to be adjacent to only the first side of the test specimen; and
    a mounting structure configured to engage only the second side of the test specimen, the mounting structure operable to maintain a position of the test specimen and substantially support the weight of the test specimen; and
    a device for creating a dynamic pressure event on the test specimen and the incompressible liquid,
    wherein the device for creating a dynamic pressure event is a dynamic hydraulic pressure supply.

11. A method of testing a circuit card for ballistic applications, the method comprising:
    providing a circuit card having a first side and a second side opposite the first side;
    providing an incompressible liquid adjacent to only the first side of the circuit card;
    engaging only the second side of the circuit card with a mounting structure; and
    creating a dynamic force on the second side of the circuit card toward the incompressible liquid,
    wherein the creating a dynamic force step includes using a vibration actuator to vibrate the circuit card relative to the incompressible liquid.

12. The method of claim 11 further comprising providing a reaction mass situated opposite the test specimen from the incompressible liquid.

13. An apparatus for simulating a dynamic high-g environment on a test specimen having a first side and a second side opposite the first side, said apparatus comprising:
    an incompressible liquid, all of said incompressible liquid of said apparatus situated to be adjacent to only the first side of the test specimen; and
    a mounting structure configured to engage only the second side of the test specimen, the mounting structure operable to maintain a position of the test specimen and substantially support the weight of the test specimen; and
    a device for creating a dynamic pressure event on the test specimen and the incompressible liquid,
    wherein the device for creating a dynamic pressure event is capable of generating at least about 1,000 pounds of force.

* * * * *